(12) United States Patent
Ford

(10) Patent No.: US 8,702,424 B2
(45) Date of Patent: Apr. 22, 2014

(54) DENTAL IMPLANT ASSEMBLY

(76) Inventor: Christopher W. Ford, Holly, MI (US)

( * ) Notice: Subject to any disclaimer, the term of this patent is extended or adjusted under 35 U.S.C. 154(b) by 144 days.

(21) Appl. No.: 12/427,006

(22) Filed: Apr. 21, 2009

(65) Prior Publication Data

US 2010/0266987 A1   Oct. 21, 2010

(51) Int. Cl.
*A61C 8/00* (2006.01)

(52) U.S. Cl.
USPC .......................................................... 433/174

(58) Field of Classification Search
USPC .............................. 433/212.1, 172–176, 201.1
See application file for complete search history.

(56) References Cited

U.S. PATENT DOCUMENTS

| | | | |
|---|---|---|---|
| 3,386,169 A * | 6/1968 | Scialom | 433/173 |
| 3,740,851 A | 6/1973 | Weissman | |
| 3,797,113 A | 3/1974 | Brainin | |
| 3,849,887 A | 11/1974 | Brainin | |
| 4,713,003 A | 12/1987 | Symington et al. | |
| 5,791,899 A * | 8/1998 | Sachdeva et al. | 433/173 |
| 6,039,568 A * | 3/2000 | Hinds | 433/175 |
| 6,743,018 B1 * | 6/2004 | Morrow | 433/173 |
| 8,011,926 B2 * | 9/2011 | Ford et al. | 433/174 |
| 2006/0204928 A1 * | 9/2006 | Hurson | 433/173 |
| 2007/0141532 A1 * | 6/2007 | Ford et al. | 433/173 |
| 2008/0286720 A1 * | 11/2008 | Reed | 433/174 |
| 2008/0286721 A1 * | 11/2008 | Walther | 433/174 |
| 2009/0208907 A1 * | 8/2009 | Dosta et al. | 433/174 |

\* cited by examiner

*Primary Examiner* — Cris L Rodriguez
*Assistant Examiner* — Mirayda A Aponte
(74) *Attorney, Agent, or Firm* — Dickinson Wright PLLC

(57) ABSTRACT

A dental implant assembly (20) for transferring forces from a tooth replicating device (22) to a bone (24) of a person. The implant (26) has an exterior surface (32) defining an abutment portion (36) for engaging the tooth replicating device (22) to receive the forces and a lower portion (34) axially below the abutment portion (36) for engaging the bone (24). A collar (38) is disposed about and extends radially outwardly from the lower portion (34) for engaging the bone (24) and for transferring the forces from the implant (26) to the bone (24). The implant (26) defines an inner pocket (48) extending along the axis (A), and a rod (50) is disposed in the inner pocket (48) of the implant (26) and extends along the axis (A) between the lower and abutment portions (34, 36) for transferring the forces received by the abutment portion (36) to the collar (38) disposed about the lower portion (34).

14 Claims, 1 Drawing Sheet

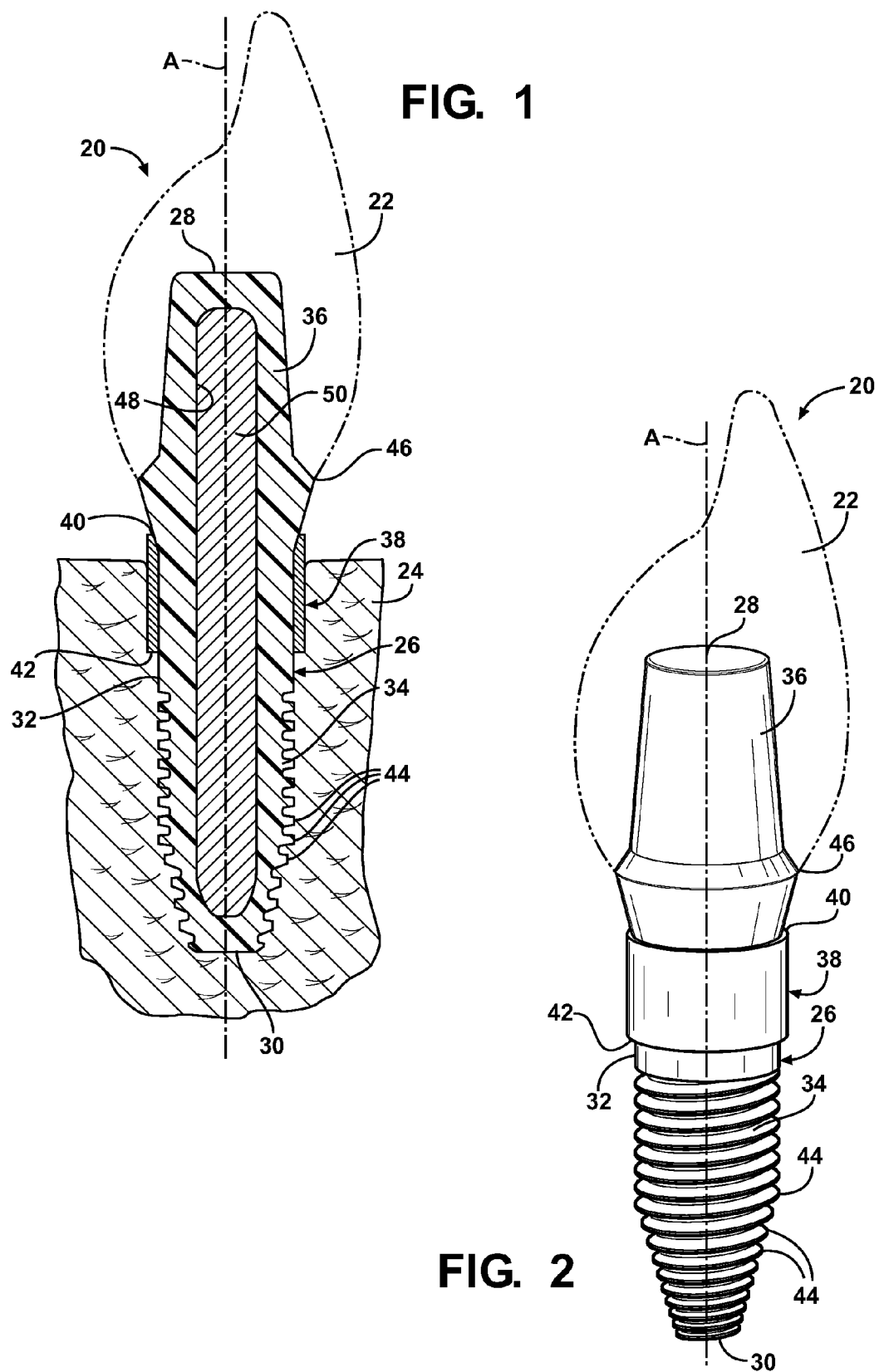

DENTAL IMPLANT ASSEMBLY

BACKGROUND OF THE INVENTION

1. Field of the Invention

The subject invention relates to a dental implant assembly for transferring forces from a tooth replicating device to a bone of a person.

2. Description of the Prior Art

U.S. Pat. No. 3,849,887, issued to Herbert Brainin on Nov. 26, 1974, shows such a dental implant assembly including an implant extending along an axis. The implant has an exterior surface defining an abutment portion for engaging the tooth replicating device to receive the forces from the tooth replicating device and a lower portion axially below the abutment portion for engaging the bone. The implant includes an inner pocket extending along the axis.

U.S. patent application Ser. No. 12/120,809, assigned to the inventors herein, shows a collar disposed about and extending radially outwardly from the lower portion of an implant for engaging the bone and for transferring the forces from the implant to the bone.

SUMMARY OF THE INVENTION AND ADVANTAGES

The invention provides for such a dental implant assembly and including a rod disposed in the inner pocket of the implant and extending along the axis between the abutment and lower portions for transferring forces received by the abutment portion to the collar disposed about the lower portion.

The rod reinforces the implant to allow the implant to be made of a cheaper, weaker material. In operation, e.g. when the person bites, the tooth replicating device sends forces through the abutment portion of the implant to the rod disposed in the implant. The rod, then distributes the forces to the lower portion of the implant and on to the collar disposed about the lower portion of the implant. The collar then dispenses the forces to the bone of the person.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 1 is a cross-sectional view of the dental implant assembly in an installed state, and FIG. 2 is a perspective view of the dental implant assembly.

DETAILED DESCRIPTION OF THE EXEMPLARY EMBODIMENT

Referring to the Figures, wherein like numerals indicate corresponding parts throughout the several views, the invention is a dental implant assembly 20 for transferring forces from a tooth replicating device 22 to a bone 24 of a person.

The dental implant assembly 20, generally shown, includes a one-piece implant 26, generally indicated, extending along an axis A from an implant top end 28 to an implant bottom end 30. The implant 26 is made of a first material fracturable in response to a predetermined force. In the exemplary embodiment, the first material of the implant 26 is polyetheretherketone (PEEK), which is a polymeric material. The implant 26 could also be coated with a bone 24 growth stimulant, such as hydroxyapatite.

The implant 26 has an exterior surface 32 defining a lower portion 34 and an abutment portion 36. The lower portion 34 is disposed axially below the abutment portion 36. As best shown in FIG. 2, the abutment portion 36 of the implant 26 is for engaging the tooth replicating device 22, or the crown, to receive the forces from the tooth replicating device 22. Preferably, the tooth replicating device 22 is cemented onto the abutment portion 36 of the implant 26, but any other means may be used to attach the tooth replicating device 22 to the abutment portion 36 of the implant 26. The lower portion 34 is for engaging the bone 24 of the person. The lower portion 34 of the implant 26 has a circular cross-section decreasing in size from the abutment portion 36 to the implant bottom end 30.

A collar 38, generally indicated, is disposed about and extends radially outwardly from the lower portion 34 of the implant 26. The collar 38 extends axially from a collar top end 40 adjacent the abutment portion 36 to a collar bottom end 42 spaced from the implant bottom end 30. When installed in the bone 24 of the person, the collar 38 engages the bone 24 and transfers the forces from the implant 26 to the bone 24. The collar 38 is made of a second material fracturable only in response to a force greater than the predetermined force. In the exemplary embodiment, the second material of the collar 38 being a metal, preferably titanium or a titanium alloy. The collar 38 is preferably made of titanium because of its biocompatibility properties, but may be made of any other material capable of transferring forces from the implant 26 to the bone 24 of the person.

The exterior surface 32 of the lower portion 34 of the implant 26 defines self tapping threads 44 extending from the collar bottom end 42 to the implant bottom end 30 for threading into the bone 24.

As best shown in FIG. 1, the abutment portion 36 of the implant 26 has a circular cross-section increasing in size from the collar top end 40 to a larger belt 46 and decreasing in size from the larger belt 46 to the implant top end 28 for supporting the tooth replicating device 22.

The implant 26 further defines an inner pocket 48 extending along the axis A. As best shown in FIG. 1, the inner pocket 48 of the implant 26 extends axially between the abutment and lower portions 36, 34. A rod 50 is disposed in the inner pocket 48 of the implant 26 and extends along the axis A from the abutment portion 36 to the lower portion 34 and axially past the collar 38 for transferring the forces received by the abutment portion 36 to the collar 38 disposed about the lower portion 34 and to the lower portion 34 of the implant 26 below the collar 38. The rod 50 is of a third material fracturable only in response to a force greater than the predetermined force. In the exemplary embodiment, the third material of the rod 50 is a chromium cobalt alloy, but may be made of any other material fracturable only in response to a force greater than the predetermined force.

Obviously, many modifications and variations of the present invention are possible in light of the above teachings and may be practiced otherwise than as specifically described while within the scope of the appended claims. That which is prior art in the claims precedes the novelty set forth in the "characterized by" clause. The novelty is meant to be particularly and distinctly recited in the "characterized by" clause whereas the antecedent recitations merely set forth the old and well-known combination in which the invention resides. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the"

What is claimed is:

1. A dental implant assembly (20) for transferring forces from a tooth replicating device (22) to a bone (24) of a person comprising:
   an implant (26) formed as one integral piece of material and extending along an axis (A),
   said implant (26) having an exterior surface (32) defining an abutment portion (36) for engaging the tooth replicating device (22) to receive the forces from the tooth replicating device (22) and a lower portion (34) axially below said abutment portion (36) for engaging the bone (24),
   a collar (38) disposed about and extending radially outwardly from said lower portion (34) of said one-piece implant (26) for engaging the bone (24) and for transferring the forces from said implant (26) to the bone (24),
   said implant (26) defining an inner pocket (48) extending along said axis (A),
   and characterized by
   a rod (50) disposed in said inner pocket (48) and encapsulated within said implant (26) and extending along said axis (A) from said abutment portion (36) to said lower portion (34) and axially past said collar (38) for transferring forces received by said abutment portion (36) to said collar (38) and to said lower portion (34) below said collar (38), and
   said collar (38) being formed as a separate piece of material from said one-piece implant (26) and following a contour of a portion of said exterior surface (32) of said one-piece implant (26) between a collar top end (40) surface and a collar bottom end (42) surface.

2. The assembly as set forth in claim 1 wherein said implant (26) is of a first material fracturable in response to a predetermined force,
   said collar (38) is of a second material and said rod (50) is of a third material, and
   said second and third materials are fracturable only in response to a force greater than said predetermined force.

3. The assembly as set forth in claim 2 wherein said first material of said implant (26) is a polymeric material.

4. The assembly as set forth in claim 3 wherein said polymeric material of said implant (26) is further defined as polyetheretherketone.

5. The assembly as set forth in claim 2 wherein said second material of said collar (38) is a metal.

6. The assembly as set forth in claim 5 wherein said metal of said collar (38) is further defined as titanium.

7. The assembly as set forth in claim 2 wherein said third material of said rod (50) is a metal.

8. The assembly as set forth in claim 7 wherein said metal of said rod (50) is further defined as a chromium cobalt alloy.

9. The assembly as set forth in claim 1 wherein said implant (26) extends axially from an implant top end (28) to an implant bottom end (30).

10. The assembly as set forth in claim 9 wherein said lower portion (34) of said implant (26) has a circular cross-section decreasing in size from said abutment portion (36) to said implant bottom end (30).

11. The assembly as set forth in claim 9 wherein said collar (38) extends axially from a collar top end (40) adjacent said abutment portion (36) to a collar bottom end (42) spaced from said implant bottom end (30).

12. The assembly as set forth in claim 11 wherein said abutment portion (36) of said implant (26) has a circular cross-section increasing in size from said collar top end (40) to a larger belt (46) and decreasing in size from said larger belt (46) to said implant top end (28) for supporting the tooth replicating device (22).

13. The assembly as set forth in claim 1 wherein said exterior surface (32) of said lower portion (34) of said implant (26) defines self tapping threads (44) for threading into the bone (24).

14. A dental implant assembly (20) for transferring forces from a tooth replicating device (22) to a bone (24) of a person comprising:
   a one-piece implant (26) extending along an axis (A) from an implant top end (28) to an implant bottom end (30),
   said implant (26) being of a first material fracturable in response to a predetermined force,
   said first material of said implant (26) being a polymeric material,
   said polymeric material of said implant (26) being further defined as polyetheretherketone,
   said implant (26) having an exterior surface (32) defining an abutment portion (36) for engaging the tooth replicating device (22) to receive the forces from the tooth replicating device (22) and a lower portion (34) axially below said abutment portion (36) for engaging the bone (24),
   said lower portion (34) of said implant (26) having a circular cross-section decreasing in size from said abutment portion (36) to said implant bottom end (30),
   a collar (38) disposed about and extending radially outwardly from said lower portion (34) of said implant (26) and extending axially from a collar top end (40) adjacent said abutment portion (36) to a collar bottom end (42) spaced from said implant bottom end (30) for engaging the bone (24) and for transferring the forces from said implant (26) to the bone (24),
   said collar (38) being of a second material fracturable only in response to a force greater than said predetermined force,
   said second material of said collar (38) being a metal,
   said metal of said collar (38) being further defined as titanium,
   said exterior surface (32) of said lower portion (34) of said implant (26) defining self tapping threads (44) extending from said collar bottom end (42) to said implant bottom end (30) for threading into the bone (24),
   said abutment portion (36) of said implant (26) having a circular cross-section increasing in size from said collar top end (40) to a larger belt (46) and decreasing in size from said larger belt (46) to said implant top end (28) for supporting the tooth replicating device (22),
   said implant (26) defining an inner pocket (48) extending along said axis (A),
   and characterized by
   said collar (38) being formed as a separate piece of material from said one-piece implant (26) and following a contour of a portion of said exterior surface (32) of said one-piece implant (26) between a collar top end (40) surface and a collar bottom end (42) surface and said collar (38) having an outer surface extending in parallel with said axis (A) of said one-piece implant (26), said inner pocket (48) of said implant (26) extending axially between said abutment and lower portions (36, 34), a rod (50) disposed in said inner pocket (48) and encapsulated by said implant (26) and extending along said axis (A) between said abutment and lower portions (36, 34) for transferring the forces received by said abutment portion (36) to said collar (38) disposed about said lower portion (34) with said rod (50) occupying substantially all of the space of said inner pocket (48), said rod (50) being of a third material fracturable only in response to a force greater than said predetermined force, said third material of said rod (50) being a metal, said metal of said rod (50) being further defined as chromium cobalt alloy, said collar (38) being located axially between said larger belt (46) and said implant bottom end (30) and having an interior surface with a larger inner diameter at said collar top end (40) than at said collar bottom end (42).

* * * * *